US008349303B1

(12) United States Patent
Phillips et al.

(10) Patent No.: US 8,349,303 B1
(45) Date of Patent: Jan. 8, 2013

(54) POLYMERIC QUATERNIUM COMPOUNDS

(75) Inventors: Eric Phillips, Ontario, NY (US); Jay F. Kunzler, Canandaigua, NY (US); Alok Kumar Awasthi, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 304 days.

(21) Appl. No.: 12/758,860

(22) Filed: Apr. 13, 2010

Related U.S. Application Data

(60) Provisional application No. 61/173,704, filed on Apr. 29, 2009.

(51) Int. Cl.
*A61K 31/74* (2006.01)

(52) U.S. Cl. .................................................... 424/78.04

(58) Field of Classification Search ................ 424/78.02
See application file for complete search history.

(56) References Cited

U.S. PATENT DOCUMENTS

| | | | | |
|---|---|---|---|---|
| 4,217,914 | A * | 8/1980 | Jacquet et al. | 132/208 |
| 4,407,791 | A | 10/1983 | Stark | |
| 4,525,346 | A | 6/1985 | Stark | |
| 4,923,619 | A * | 5/1990 | Legros | 210/764 |
| 5,578,598 | A | 11/1996 | Abe et al. | |
| 6,051,611 | A | 4/2000 | Kyba et al. | |
| 2006/0100173 | A1* | 5/2006 | Powell et al. | 514/54 |
| 2008/0218686 | A1* | 9/2008 | Sharma et al. | 351/160 R |

* cited by examiner

*Primary Examiner* — Sreeni Padmanabhan
*Assistant Examiner* — Gigi Huang
(74) *Attorney, Agent, or Firm* — Joseph Barrera

(57) ABSTRACT

A topical pharmaceutical composition comprising a pharmaceutical active and a polymer of general formula I or general formula II

I

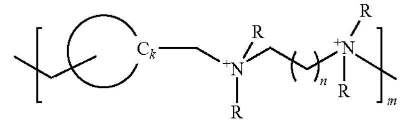

II

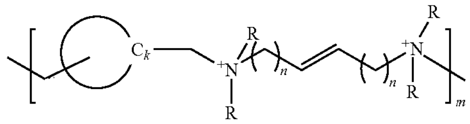

wherein $C_k$ is a saturated or unsaturated, five, six or seven-membered ring;
R is a $C_1$-$C_3$alkyl; n is 1, 2, 3, 4 or 5 and m provides a number average molecular weight of the polymer of from 2000 to 80,000.

10 Claims, No Drawings

POLYMERIC QUATERNIUM COMPOUNDS

CROSS REFERENCE

This application claims the benefit of U.S. provisional application Ser. No. 61/173,704 filed Apr. 29, 2009 under 35 U.S.C. §119(e).

The present invention relates to polymeric quaternium compounds and compositions that include the polymeric quaternium compounds

BACKGROUND OF THE INVENTION

Multi-dose pharmaceutical formulations such as a nasal spray, or an otic or ophthalmic drop formulation, that contains a pharmaceutical active typically includes a preservative agent to inhibit growth of bacteria and/or fungi if the formulation becomes contaminated with such organisms. Such preservative agents should have a broad spectrum of preservative activity and be non-irritating to biological tissues. Many preservative agents, however, have a tendency to irritate such tissues, particularly, if the agent is present at relatively high concentrations.

In addition, many dermatological products including, but not limited to cosmetic formulations, also require the presence of a preservative or antimicrobial agent. Again, such preservative agents should have a broad spectrum of preservative activity and be non-irritating to the skin.

U.S. Pat. No. 5,578,598 describes the use of a water insoluble, polyelectrolyte complex that is prepared by mixing an aqueous solution of a cationic polymer and an aqueous solution of an anionic polymer. The cationic polymer includes quaternary ammonium polymers of formula A

A

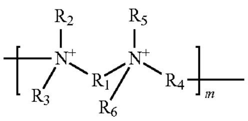

wherein $R_1$ and $R_4$ are independently a $C_1$-$C_{10}$alkylene or a disubstituted $C_8$-$C_{10}$arylene; $R_2$, $R_3$, $R_4$ and $R_5$ are independently a $C_1$-$C_3$alkyl; and m is a number from 5 to 500. The corresponding anionic polymer includes a peptide with anionic acidic sites, an acrylic acid polymer or a biopolymer with anionic sites such as hyaluronic acid, alginic acid or chondroitin sulfate. The polyelectrolyte complex is obtained as a gelatinous precipitate from the aqueous solution. The polyelectrolyte complex is said to possess antimicrobial activity if applied as a coating to almost any material substrate.

Given the requirement of preservative agents or systems in many pharmaceutical formulations, and in particular, for multi-dose formulations, there remains an interest in identifying and developing such agents with a relatively robust antimicrobial activity and a relatively low toxicity profile.

SUMMARY OF THE INVENTION

The invention is directed to a topical pharmaceutical composition comprising a pharmaceutical active and a polymer of general formula I or general formula II

I

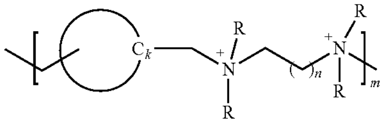

II

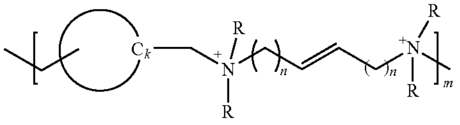

wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000.

The invention is also directed to an ophthalmic composition comprising a polymer of general formula I or general formula II

I

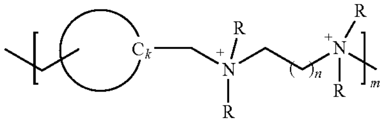

II

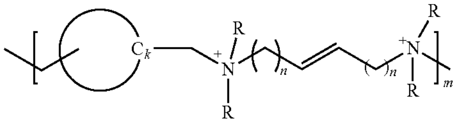

wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000. In particular, the composition is formulated as a contact lens care solution or as an eye comfort formulation.

The invention is also directed to a dermatological composition comprising a polymer of general formula I or general formula II

I

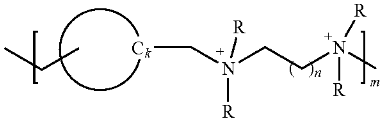

II

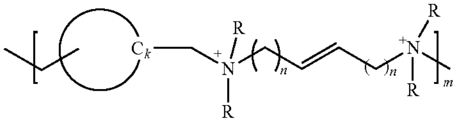

wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000, and the polymer of general formula I or general formula II is provided at a concentration of 0.5 ppm to 30 ppm.

DETAILED DESCRIPTION OF THE INVENTION

The invention is directed to a topical pharmaceutical composition comprising a pharmaceutical active and a polymer of general formula I or general formula II

I

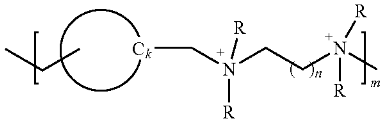

II

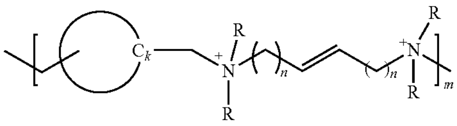

wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000.

In many of the pharmaceutical compositions, the polymer of general formula I or general formula II includes a $C_k$ selected from the group consisting of phenyl, cyclohexyl, cyclohexene and cyclopentyl. Also, in such embodiments one often finds that R is methyl, and n is 1 or 2. In one particular embodiment, $C_k$ is phenyl, R is methyl, and n is 1 or 2.

In many of the topical pharmaceutical compositions or lens care solutions, the polymer of general formula I or general formula II will typically have a number average molecular weight with a minimum value of 2000, 4000 or 6000 and a maximum value of 80,000, 60,000, 40,000 or 24,000. Accordingly, some of the more preferred number average molecular weight ranges for the polymers of general formula I or general formula II are from 2000 to 60,000, from 2000 to 40,000, from 4000 to 40,000 or from 4000 to 24,000.

In many compositions in which the polymeric quaternium compounds of general formula I or general formula II are used in a preservative effective amount, or in an antimicrobial effective amount, the polymeric quaternium compounds of general formula I or general formula II is present in the composition from 0.00005% to 0.1% by weight. In an exemplary composition, the polymeric quaternium compounds of general formula I or general formula II is present in the composition from 0.0005% to 0.05% by weight. In still other exemplary compositions, the polymeric quaternium compounds of general formula I or general formula II is present in the composition from 0.0005% to 0.005% by weight.

A "preservative-effective amount" is defined as a sufficient amount of preservative component(s), which would include the polymeric quaternium compounds of general formula I or general formula II, in the composition to reduce the cell population by two log orders after 7 days of the five following microorganisms, *Staphylococcus aureus, Pseudomonas aeruginosa, Eschrechia coli, Candida albicans* and *Aspergillus niger*, or that which will prevent the growth of fungal bioburden by ±0.5 log. The term includes amounts in the compositions in which the polymeric quaternium compounds of general formula I or general formula II are present as the sole preservative component or are present as a co-preservative component with another preservative component. In the later instance, the polymeric quaternium compounds of general formula I or general formula II are believed to complement a preservative component in the formulation. In fact, relatively small amounts the polymeric quaternium compounds of general formula I or general formula II are needed to enhance the biocidal effectiveness of the formulations, particularly against fungi, e.g., *Fusarium solani* and *Candida albicans.*

A "antimicrobial-effective amount" is defined as a sufficient amount of preservative component(s), which would include the polymeric quaternium compounds of general formula I or general formula II, in the composition to reduce the cell population by three log orders after 7 days of the five following microorganisms, *Staphylococcus aureus, Pseudomonas aeruginosa, Eschrechia coli, Candida albicans* and *Aspergillus niger*. In demonstrating the efficacy of the addition of the polymeric quaternium compounds of general formula I or general formula II, a Stand-Alone Biocidal Efficacy Test was used. The "Stand-Alone Procedure for Disinfecting Products" is based on the Disinfection Efficacy Testing for Products dated May 1, 1997, prepared by the U.S. Food and Drug Administration, Division of Ophthalmic Devices. This performance requirement does not contain a rub procedure. This performance requirement is comparable to current ISO standards for disinfection of contact lenses (revised 1995).

The stand-alone test challenges a disinfecting product with a standard inoculum of a representative range of microorganisms and establishes the extent of viability loss at predetermined time intervals comparable with those during which the product may be used. The primary criteria for a given disinfection period (corresponding to a potential minimum recommended disinfection period) is that the number of bacteria recovered per mL must be reduced by a mean value of not less than 3.0 logs within the given disinfection period. The number of mold and yeast recovered per mL must be reduced by a mean value of not less than 1.0 log within the minimum recommended disinfection time with no increase at four times the minimum recommended disinfection time.

The term, "antimicrobial-effective amount" includes amounts in the compositions in which the polymeric quaternium compounds of general formula I or general formula II are present as the sole antimicrobial component or are present as a co-disinfecting component with another antimicrobial component. In the later instance, the polymeric quaternium compounds of general formula I or general formula II are believed to complement an antimicrobial component in the composition.

For example, in addition to the polymeric quaternium compounds of general formula I or general formula II, compositions can also include a preservative component selected from other quaternium ammonium compounds (including small molecules) and polymers and low and high molecular weight biguanides. For example, biguanides include the free bases or salts of alexidine, chlorhexidine, hexamethylene biguanides and their polymers (PHMB) and any one mixture thereof. The salts of alexidine and chlorhexidine can be either organic or inorganic and include gluconates, nitrates, acetates, phosphates, sulfates, halides and the like.

In a preferred embodiment, the formulation will include a polymeric biguanide known as poly(hexamethylene biguanide) (PHMB or PAPB) commercially available from Zeneca, Wilmington, Del. under the trademark COSMOCIL® CQ. For many ophthalmic formulations, the PHMB is present in the formulations from 0.1 ppm to 5 ppm, 0.1 ppm to 2 ppm or from 0.2 ppm to 0.5 ppm.

A biguanide of interest is 1,1'-hexamethylene-bis[5-(2-ethylhexyl)biguanide], which is referred to in the art as "alexidine". Again, for an ophthalmic formulation the alexidine is most likely present in the formulation from 0.5 ppm to 5 ppm or from 0.5 ppm to 2 ppm.

One of the more common quaternium ammonium compounds is α-[4-tris(2-hydroxyethyl)-ammonium chloride-2-butenyl]poly[1-dimethyl ammonium chloride-2-butenyl]-co-tris(2-hydroxyethyl)ammonium chloride, also referred to in the art as polyquaternium-1. Quaternium ammonium compounds are generally referred to in the art as "polyquaternium" disinfectants, and are identified by a particular number following the designation such as polyquaternium-1, polyquaternium-10 or polyquaternium-42. Pin many, but not all formulations, the polyquaternium-1 is present in the formulation from 0.5 ppm to 5 ppm. Polyquaternium-42 is also one of the more preferred polyquaternium disinfectants, see, U.S. Pat. No. 5,300,296.

Still other preservative components that are used in combination with polymeric quaternium compounds of general formula I or general formula II are polylysine, hydrogen peroxide or a form of stabilized peroxide or diglycine.

As mentioned, the compositions described can be an ophthalmic composition prescribed by or recommended by a physician, or a health care provider, e.g., an O.D., to treat an ocular condition or an ocular disease.

Exemplary compositions for the treatment of dry eye are provided in Tables 1 to 4. Each component is listed as % w/w except as noted. Additional information on dry eye compositions can be found in U.S. patent application Ser. No. 11/842,394, filed Aug. 21, 2007.

TABLE 1

| Component | % w/w |
|---|---|
| Carbopol ® 980NF | 0.02 to 0.2 |
| glycerin | 0.01 to 0.5 |
| Example No. 1 | 0.0001 to 0.005 |
| sorbitol | 0.5 to 5.0 |
| purified water | q.s. to 100% |

Another ophthalmic composition is a sterile, buffered, hypotonic solution intended for use as an artificial tear and lubricant for providing soothing therapy to dry irritated eyes, Table 2. The solution is a non-blurring, low viscosity liquid that contains propylene glycol and glycerin as demulcents. The solution also contains alginate, which is a biopolymer believed to interact with the mucin layer to help to keep the tear film intact, and to provide long term relief to the dry eyes.

TABLE 2

| Component | % w/w |
|---|---|
| Protanal LF200M alginate | 0.05 to 0.5 |
| glycerin | 0.1 to 1.0 |
| propylene glycol | 0.1 to 1.0 |
| Example No. 1 | 0.0001 to 0.005 |
| sodium borate | 0.01 to 0.04 |
| boric acid | 0.2 to 0.8 |
| Dequest ® 2016 | 0.02 to 1.2 |
| purified water, USP | Q.S. to 100% |

TABLE 3

| Component | % w/w |
|---|---|
| hydroxyethyl cellulose or hydroxypropyl guar | 0.2 to 2.0 |
| propylene glycol | 2.0 to 20 |
| Example No. 1 | 0.0001 to 0.005 |
| Polyquaternium-1 (ppm) | 2 to 15 |
| EDTA | 0.2 to 1.5 |
| purified water, USP | Q.S. to 100% |

The pharmaceutical active can be any compound that is used to treat any one disease or any one medical condition. As used herein, the term "pharmaceutical active" refers to a compound, or a mixture of compounds, that when administered to a subject (human or animal) causes a desired pharmacologic and/or physiologic effect by local and/or systemic action. Accordingly, pharmaceutical compositions comprising the polymeric quaternium compounds of general formula I or general formula II have the benefit of being adequately preserved without having a harsh physiological effect such as irritation or discomfort, which is common with many preservative agents.

Accordingly, the pharmaceutical agent can be selected from any one class of compounds, for example, anti-inflammatory agents, anti-infective agents (including, but not limited to antibacterial, antifungal, antiviral, antiprotozoal agents), anti-allergic agents, antiproliferative agents, anti-angiogenic agents, anti-oxidants, antihypertensive agents, neuroprotective agents, cell receptor agonists, cell receptor antagonists, immunomodulating agents, immunosuppressive agents, IOP lowering agents, beta adrenoceptor antagonists, alpha-2 adrenoceptor agonists, carbonic anhydrase inhibitors, cholinergic agonists, prostaglandins and prostaglandin receptor agonists, angiotensin converting enzyme ("ACE") inhibitors, AMPA receptor antagonists, NMDA antagonists, angiotensin receptor antagonists, somatostatin agonists, mast cell degranulation inhibitors, alpha-adrenergic receptor blockers, alpha-2 adrenoceptor antagonists, thromboxane A2 mimetics, protein kinase inhibitors, prostaglandin F derivatives, prostaglandin-2 alpha antagonists, cyclooxygenase-2 inhibitors and muscarinic agents.

Of particular interest are pharmaceutical active agents that are known to treat an ocular disease or disorder including, but are not limited to, a posterior-segment disease or disorder. In certain embodiments, such disease or disorder is selected from the group consisting of diabetic retinopathy, diabetic macular edema, cystoid macular edema, age macular degeneration (including the wet and dry form), optic neuritis, retinitis, chorioretinitis, intermediate and posterior uveitis and choroidal neovascuralization.

Glaucoma is a group of diseases that are characterized by the death of retinal ganglion cells ("RGCs"), specific visual field loss, and optic nerve atrophy. Glaucoma is the third leading cause of blindness worldwide. An intraocular pressure ("IOP") that is high compared to the population mean is a risk factor for the development of glaucoma. However, many individuals with high IOP do not have glaucomatous loss of vision. Conversely, there are glaucoma patients with normal IOP. Therefore, continued efforts have been devoted to elucidate the pathogenic mechanisms of glaucomatous optic nerve degeneration.

It has been postulated that optic nerve fibers are compressed by high IOP, leading to an effective physiological axotomy and problems with axonal transport. High IOP also results in compression of blood vessels supplying the optic nerve heads ("ONHs"), leading to the progressive death of RGCs. See; e.g., M. Rudzinski and H. U. Saragovi, *Curr. Med. Chem.-Central Nervous System Agents*, Vol. 5, 43 (2005).

In one embodiment, the anti-glaucoma pharmaceutical agent is of general formula III

III

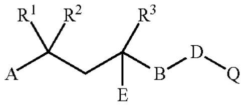

wherein A and Q are independently selected from the group consisting of aryl and heteroaryl groups substituted with at least a halogen atom, cyano group, hydroxy group, or $C_1$-$C_{10}$ alkoxy group; $R^1$, $R^2$, and $R^3$ are independently selected from the group consisting of unsubstituted and substituted $C_1$-$C_5$ alkyl groups; B is a $C_1$-$C_5$ alkylene group; D is the —NH— or —NR'— group, wherein R' is a $C_1$-$C_5$ alkyl group; and E is the hydroxy group.

Exemplary, pharmaceutical agents of general formula III include A as a dihydrobenzofuranyl group substituted with a fluorine atom; Q as a quinolinyl or isoquinolinyl group substituted with a methyl group; $R^1$ and $R^2$ are independently selected from the group consisting of unsubstituted and substituted $C_1$-$C_5$ alkyl groups; B is a $C_1$-$C_3$ alkylene group; D is the —NH— group; E is a hydroxy group; and $R^3$ is a trifluoromethyl group. Exemplary compounds include a glucocorticoid receptor agonist having Formulae III or IV, as disclosed in US Patent Application Publication 2006/0116396.

IV

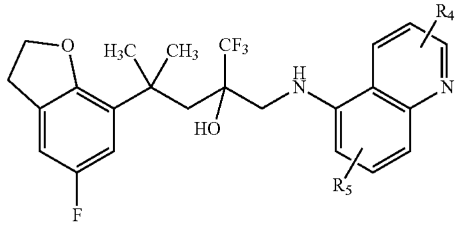

V

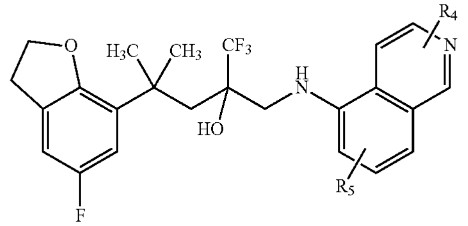

wherein $R^4$ and $R^5$ are independently selected from the group consisting of hydrogen, halogen, cyano, hydroxy, $C_1$-$C_{10}$ (alternatively, $C_1$-$C_5$ or $C_1$-$C_3$)alkoxy groups, unsubstituted $C_1$-$C_{10}$ (alternatively, $C_1$-$C_5$ or $C_1$-$C_3$) linear or branched alkyl groups, substituted $C_1$-$C_{10}$ (alternatively, $C_1$-$C_5$ or $C_1$-$C_3$) linear or branched alkyl groups, unsubstituted $C_3$-$C_{10}$ (alternatively, $C_3$-$C_6$ or $C_3$-$C_5$) cyclic alkyl groups, and substituted $C_3$-$C_{10}$ (alternatively, $C_3$-$C_6$ or $C_3$-$C_5$) cyclic alkyl groups.

Another embodiment includes ocular formulations prescribed by or recommended by a physician, or a health care provider, to treat an ocular allergic conditions. Allergy is characterized by a local or systemic inflammatory response to allergens. Allergic conjunctivitis is a disorder that is characterized by the clinical signs and symptoms of eye itching, redness, tearing, and swelling. An estimated 20% of the population in the United States suffer from inflammation of the eye. The signs and symptoms of allergic conjunctivitis can significantly impact the quality of life of patients, from social interactions, productivity at work and school, to the ability to perform visual tasks such as working on a computer or reading.

Currently, available pharmaceutical treatments for inflammation of the eye or symptoms of inflammation of the eye include (1) antihistamines, (2) drugs that block the release of histamine and other substances from the mast cell (e.g., mast cell stabilizers), (3) drugs with multiple modes of action (e.g. antihistamine/mast cell stabilizing agents), and (4) drugs that can actively constrict blood vessels thus reducing redness and swelling (e.g., vasoconstrictors). Additionally, artificial tears have been used to wash the eye of allergens.

The desirability of a particular treatment for inflammation of the eye can be measured against the following factors (1) efficacy at onset of action, (2) duration of action, (3) efficacy at controlling signs and symptoms of allergic conjunctivitis, and (4) comfort of the drop when instilled in the eye.

In still another aspect, the formulation comprising: (a) ketotifen or a salt thereof in a concentration of from a 0.001% to 0.2% (weight/volume or "w/v"); (b) naphazoline or a salt thereof in a concentration of from 0.001% to 0.2% (w/v); and (c) water.

Ketotifen or any ophthalmically acceptable ketotifen salt may be used in the method herein described, although ketotifen fumarate is preferred. Ketotifen fumarate is represented by the following formula:

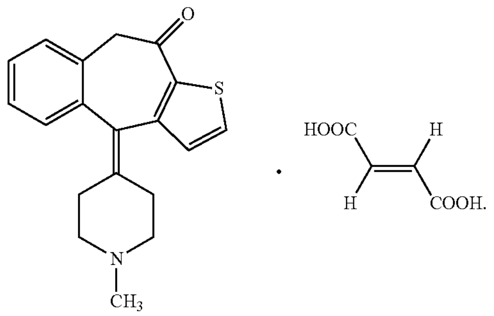 [SMILES: CN1CCC(=C2c3ccccc3CC(=O)c3sccc32)CC1 ; O=C(O)/C=C/C(=O)O]

Ketotifen or a ketotifen salt is present in a formulation in a concentration from 0.001% to 0.2% (or alternatively, from 0.001% to 0.1%). In one embodiment, ketotifen or a ketotifen salt is present in a concentration from 0.01% to 0.05%; preferably, from 0.01% to 0.04%; more preferably, from 0.02% to 0.03%. Concentrations of ketotifen salts yielding such concentrations of ketotifen may be readily calculated; for example, using ketotifen fumarate in a concentration of 0.0345% provides a concentration of ketotifen in the formulation of 0.025%.

Another embodiment is directed to an ocular formulation that includes an anti-redness agent, which may relieve redness in the eye. The preferred anti-redness agent is naphazoline or an ophthalmically acceptable salt thereof such as, for example, naphazoline hydrochloride. Other anti-redness agents that may be used include, but are not limited to, tetrahydrozoline, ephedrine, phenylephrine, oxymetazoline, xylometazoline, pseudoephedrine, tramazoline, other vasoconstrictors, combinations thereof, as well as ophthalmically acceptable salts thereof (e.g., tetrahydrozoline hydrochloride).

Naphazoline hydrochloride is represented by the following formula:

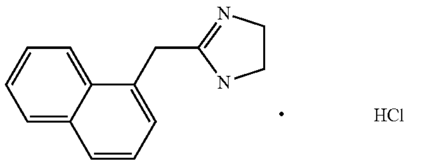

Naphazoline or a naphazoline salt may be present in a composition produced a method of the present invention in a concentration from 0.001% to 0.2% (or alternatively, from 0.001% to 0.1%). In one embodiment, naphazoline or a naphazoline salt is present in a composition at a concentration from 0.01% to 0.1%; preferably, from 0.01% to 0.07%; more preferably, from 0.02% to 0.06%. Concentrations of a naphazoline salt yielding such concentrations of naphazoline base may be readily calculated; for example, using naphazoline hydrochloride in a concentration of about 0.025% provides a concentration of naphazoline base in the formulation of 0.021%. Additional information on formulations containing ketotifen, naphazoline or a corresponding pharmaceutically salt of each thereof can be found in U.S. patent application Ser. No. 10/972,571, filed Oct. 25, 2005.

The pharmaceutical formulations will typically include tonicity agents, e.g., salts such as NaCl, to approximate the osmotic pressure of normal lachrymal fluids, which, as stated in U.S. Pat. No. 6,274,626, is equivalent to a 2.5% solution of glycerol. Osmotic pressure, measured as osmolality, is generally about 225 to 400 mOsm/kg for conventional ophthalmic formulations. In some embodiments, however, the pharmaceutical formulation may be formulated to osmolality in the range from about 400 to about 875 mOsm/kg, for some desired purposes. For example, co-assigned U.S. Patent Application No. 2006/0148899, incorporated herein by reference in its entirety, provides for ophthalmic formulations having osmolality from 400 to 875 mOsm/kg, which have been found still to provide comfort to a user.

Another embodiment is directed to a pharmaceutical formulation prescribed by or recommended by a physician, or a health care provider, to treat a dermatological condition or a dermatological disease. For example, it is known that compounds of the FK506 class can be formulated into stable emulsions. Emulsions, since they contain an aqueous phase, are much less occlusive than oil-based compositions and hence are better tolerated in many situations. Accordingly, in one embodiment a topical formulation, in the form of an emulsion, comprises a compound of the FK506 class, a physiologically acceptable alkanediol, ether diol or diether alcohol containing up to 8 carbon atoms as solvent for the compound of the FK506 class and one or more alkyldimonium hydroxypropyl alkylglucosides as a preservative agent. A compound of the "FK506 class" is a compound which has the basic structure as FK506 and which has at least one of the biological properties of FK506 (e.g., immunosuppressant properties). The compound may be in free base form or pharmaceutically acceptable, acid addition, salt form. A preferred compound of the FK 506 class is disclosed in EP 427 680, e.g. Example 66a (also called 33-epi-chloro-33-desoxyascomycin).

Contact Lens Care Solutions

The invention is also directed to a contact lens care solutions that include a polymer of general formula I or general formula II

I

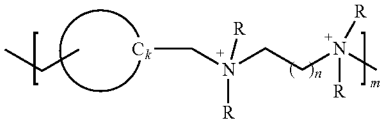

II

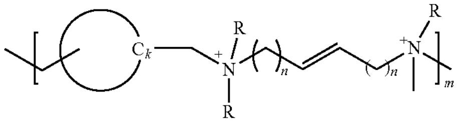

wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000. In particular, the composition is formulated as a multipurpose lens care solution or as an eye drop, comfort formulation, e.g., to treat a patient diagnosed with dry-eye syndrome or as a contact lens rewet eye drop.

In many of the lens care compositions, the polymer of general formula I or general formula II includes a $C_k$ selected from the group consisting of phenyl, cyclohexyl, cyclohexene and cyclopentyl. Also, in such embodiments one often finds that R is methyl, and n is 1 or 2. In one particular embodiment, $C_k$ is phenyl, R is methyl, and n is 1 or 2.

As stated earlier, in many of the lens care solutions, the polymer of general formula I or general formula II will typically have a number average molecular weight of with a minimum value of 2000, 4000 or 6000 and a maximum value of 80,000, 60,000, 40,000 or 24,000. Accordingly, some of the more preferred number average molecular weight ranges for the polymers of general formula I or general formula II are from 2000 to 60,000, from 2000 to 40,000, from 4000 to 40,000 or from 4000 to 24,000.

In many compositions the polymeric quaternium compounds of general formula I or general formula II are present in the composition from 0.5 ppm to 50 ppm, from 0.5 ppm to 30 ppm or from 0.5 ppm to 10 ppm.

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8.5, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate (NaH2PO$_4$) and potassium monobasic phosphate (KH2PO$_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, 2-amino-2-hydroxymethyl-1,3-propanediol (TRIS), and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1M. The borate buffer (in total) is used at a concentration of 0.02 to 0.8 M, preferably 0.07 to 0.2 M.

The lens care solutions can also include an effective amount of a surfactant component, a viscosity inducing or thickening component, a chelating or sequestering component, or a tonicity component. The additional component or components can be selected from materials which are known to be useful in contact lens care solutions and are included in amounts effective to provide the desired functional characteristic.

The amphoteric surfactants of general formula I are surface-active compounds with both acidic and alkaline properties. The amphoteric surfactants of general formula VI include a class of compounds known as betaines. The betaines are characterized by a fully quaternized nitrogen atom and do not exhibit anionic properties in alkaline solutions, which means that betaines are present only as zwitterions at near neutral pH.

VI

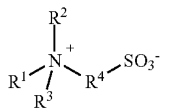

wherein $R^1$ is R or —$(CH_2)_n$—NHC(O)R, wherein R is a $C_8$-$C_{16}$alkyl optionally substituted with hydroxyl and n is 2, 3 or 4; $R^2$ and $R^3$ are each independently selected from methyl, ethyl, propyl or iso-propyl; and $R^4$ is a $C_2$-$C_8$ alkylene optionally substituted with hydroxyl.

All betaines are characterized by a fully quaternized nitrogen. In alkyl betaines, one of the alkyl groups of the quaternized nitrogen is an alkyl chain with eight to sixteen carbon atoms. One class of betaines is the sulfobetaines or hydroxysulfobetaines in which the carboxylic group of alkyl betaine is replaced by sulfonate. In hydroxysulfobetaines a hydroxy-group is positioned on one of the alkylene carbons that extend from the quaternized nitrogen to the sulfonate. In alkylamido betaines, an amide group is inserted as a link between the hydrophobic $C_8$-$C_{16}$alkyl chain and the quaternized nitrogen.

Certain sulfobetaines of general formula VI are more preferred than others. For example, Zwitergent®3-10 available from Calbiochem Company, is a sulfobetaine of general formula I wherein $R^1$ is a straight, saturated alkyl with ten (10) carbons, $R^2$ and $R^3$ are each methyl and $R^4$ is —$CH_2CH_2CH_2$— (three carbons, (3)). Other sulfobetaines that can be used in the ophthalmic compositions include the corresponding Zwitergent®3-08 ($R^1$ is a is a straight, saturated alkyl with eight carbons), Zwitergent®3-12 (R' is a is a straight, saturated alkyl with twelve carbons), Zwitergent®3-14 ($R^1$ is a is a straight, saturated alkyl with fourteen carbons) and Zwitergent®3-16 (R' is a is a straight, saturated alkyl with sixteen carbons). Accordingly, some of the more preferred the ophthalmic composition will include a sulfobetaine of general formula VI wherein $R^1$ is a $C_8$-$C_{16}$alkyl and $R^2$ and $R^3$ is methyl.

In another embodiment, the amphoteric surfactant of general formula VI is a hydroxysulfobetaine such that $R^1$ is a $C_8$-$C_{16}$alkyl substituted with at least one hydroxyl; $R^2$ and $R^3$ are each independently selected from methyl, ethyl, propyl or iso-propyl; and $R^4$ is a $C_2$-$C_8$alkylene substituted with at least one hydroxyl.

In another embodiment, the amphoteric surfactant is an alkylamido betaine of general formula VII

VII

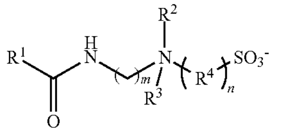

wherein $R^1$ is a $C_8$-$C_{16}$alkyl, and m and n are independently selected from 2, 3, 4 or 5; $R^2$ and $R^3$ are each independently selected from a $C_1$-$C_4$alkyl optionally substituted with hydroxyl; and $R^4$ is a $C_2$-$C_8$alkylene optionally substituted with hydroxyl. The most common alkylamido betaines are alkylamidopropyl betaines, e.g., cocoamidopropyl dimethyl betaine and lauroyl amidopropyl dimethyl betaine.

Another preferred surfactant class are the nonionic surfactants. The surfactant should be soluble in the lens care solution and non-irritating to eye tissues. Many nonionic surfactants comprise one or more chains or polymeric components having oxyalkylene (—O—R—) repeats units wherein R has 2 to 6 carbon atoms. Preferred non-ionic surfactants comprise block polymers of two or more different kinds of oxyalkylene repeat units, which ratio of different repeat units determines the HLB of the surfactant. Satisfactory non-ionic surfactants include polyethylene glycol esters of fatty acids, e.g. coconut, polysorbate, polyoxyethylene or polyoxypropylene ethers of higher alkanes ($C_{12}$-$C_{18}$). Examples of this class include polysorbate 20 (available under the trademark Tween® 20), polyoxyethylene (23) lauryl ether (Brij® 35), polyoxyethyene (40) stearate (Myrj®52), polyoxyethylene (25) propylene glycol stearate (Atlas® G 2612). Still another preferred surfactant is tyloxapol.

A particular non-ionic surfactant consisting of a poly(oxypropylene)-poly(oxyethylene) adduct of ethylene diamine having a molecular weight from about 6,000 to about 24,000 daltons wherein at least 40 weight percent of said adduct is poly(oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 904, poloxamine 1107, poloxamine 1304 or any one mixture of the three poloxamines. The foregoing poly(oxyethylene)poly(oxypropylene) block polymer surfactants will generally be present in a total amount from 0.0 to 2% w/v, from 0. to 1% w/v, or from 0.2 to 0.8% w/v.

One embodiment of particular interest is a lens care solution that specifically includes a poloxamine surfactant with a HLB value from 12 to 16.

An analogous of series of surfactants, for use in the lens care solutions, is the poloxamer series which is a poly(oxyethylene)poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene)poly(oxypropylene) block polymer surfactants will generally be present in a total amount from 0.0 to 2% w/v, from 0. to 1% w/v, or from 0.2 to 0.8% w/v.

The lens care solutions can also include one or more comfort or cushioning components. The comfort component can enhance and/or prolong the cleaning and wetting activity of the surfactant component and/or condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include hydroxypropyl guar, propylene glycol or glycerin. The comfort components are typically present in the solution from 0.01% to 1% (w/v).

One preferred comfort agent is hyaluronic acid, which is a linear polysaccharide (long-chain biological polymer) formed by repeating disaccharide units consisting of D-glucuronic acid and N-acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

The contact lens care solutions can also include PG-alginate. PG-alginate is an ester of alginic acid, which is derived from sea kelp. A portion of the carboxyl groups are esterified with propylene glycol, and a portion are neutralized with an alkali.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The contact lens care solutions can also include ϵ-polylysine, which is a homo-polypeptide of about 25 to 30 l-lysine residues. The ϵ-polylysine can also provide an additional antimicrobial affect as it has been reported that ϵ-polylysine is absorbed electrostatically to the cell surface of the bacteria, followed by a stropping of the outer membrane and eventual disruption of the cytoplasm and cell death. Commercial sources of ϵ-polylysine are obtained from biofermentation of *Streptomyces* strains.

Another preferred comfort agent that is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone. The PVP will preferably have a weight average molecular weight from 10,000 to 250,000 or from 30,000 to 100,000. Such materials are sold by various companies, including ISP Technologies, Inc. under the trademark PLASDONE®K-29/32, from BASF under the trademark KOLLIDON®, for example, KOLLIDON® K-30 or K-90. It is also preferred that one use pharmaceutical grade PVP.

The lens care solutions can also include one or more dipeptides. The dipeptide comprises a glycine moiety and another amino acid moiety other than glycine, or diglycine The dipeptide or dyglycine is present in the lens care solution from 0.01 wt. % to 1.0 wt. %. Additional information on these dipeptides can be found in U.S. patent application Ser. No. 12/054,577 filed Mar. 28, 2008 and assigned to Bausch & Lomb, Incorporated, Rochester, N.Y.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$. Other chelating components include citric acid and its salts or succinic acid and its salts.

The lens care solutions can also include a phosphonic acid, or its physiologically compatible salt, that is represented by the following formula:

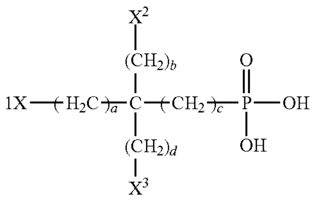

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

One possible alternative to the chelator $Na_2EDTA$ or a possible combination with $Na_2EDTA$, is a disuccinate of formula IV below or a corresponding salt thereof;

IV

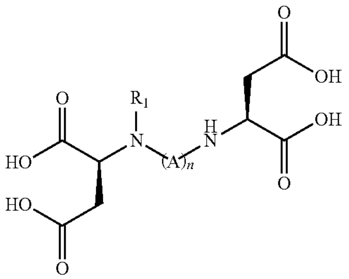

wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S-ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmolfkg for example, about 300 or about 350 to about 400 mOsmoUkg. The lens care solutions are substantially isotonic or hypertonic (for example, slightly hypertonic) and are ophthalmically acceptable.

Exemplary lens care solutions are formulated as a contact lens disinfecting solution prepared with the components and amounts of each listed in Table 4. Amounts are provided in wt. % unless otherwise noted (e.g., in ppm).

TABLE 4

| Component | minimum amount (wt. %) | maximum amount (wt. %) | preferred amount (wt. %) |
|---|---|---|---|
| boric acid | 0.10 | 1.0 | 0.64 |
| sodium borate | 0.01 | 0.20 | 0.1 |
| sodium chloride | 0.20 | 0.80 | 0.49 |
| Example 1 (ppm) | 0.5 | 20 | 10 |
| Tetronic ® 1107 | 0.05 | 2.0 | 1.00 |
| $Na_2EDTA$ | 0.005 | 0.15 | 0.03 |
| PHMB (ppm) | 0.2 | 2 | 0.6 |

Another contact lens solution includes the following ingredients listed in Table 5.

TABLE 5

| Component | minimum amount (wt.%) | maximum amount (wt.%) | preferred amount (wt.%) |
|---|---|---|---|
| sorbitol or xylitol | 0.5 | 5 | 3 |
| poloxamer 407 | 0.05 | 1.0 | 0.10 |
| sodium phosphate, dihydrogen | 0.10 | 0.8 | 0.46 |
| dexpanthenol | 0.01 | 1.0 | 0.03 |
| sorbitol | 0.1 | 1.0 | 0.4 |
| Example 1 (ppm) | 0.5 | 20 | 10 |
| $Na_2EDTA$ | 0.005 | 0.3 | 0.05 |
| PHMB (ppm) | 0.2 | 2 | 0.6 |

Another contact lens solution includes the following ingredients listed in Table 6.

TABLE 6

| Component | minimum amount (wt.%) | maximum amount (wt.%) | preferred amount (wt.%) |
|---|---|---|---|
| NaCl/KCl | 0.01 | 0.5 | 0.10 |
| propylene glycol | 0.2 | 2.0 | 0.6 |
| Tetronic ® 1304 | 0.01 | 0.2 | 0.05 |
| boric acid | 0.1 | 1.0 | 0.60 |
| sodium borate | 0.01 | 0.2 | 0.10 |
| hydroxypropyl guar | 0.01 | 0.5 | 0.05 |
| Example 1 (ppm) | 0.5 | 20 | 10 |
| $Na_2EDTA$ | 0.02 | 0.1 | 0.05 |
| polyquaternium-1 (ppm) | 1 | 10 | 3 |

As described, the lens care solutions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is then removed from the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The lens care solutions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

The lens care solutions can also be formulated as a contact lens rewetting eye drop solution. By way of example, the rewetting drops may be formulated according to any one of the foregoing formulations of Tables 1 to 3 above. Alternatively, the formulations may be modified by increasing the amount of surfactant; by reducing the amount of antimicrobial agent to a preservative amount and/or by adding a humectant and/or demulcent.

Dermatological Compositions

The invention is also directed to a dermatological composition comprising a polymer of general formula I or general formula II

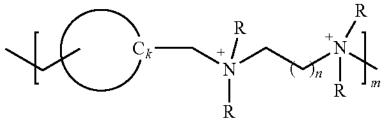
I

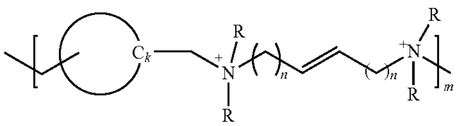
II wherein $C_k$ is a saturated or unsaturated, five, six or seven-membered ring;

R is a $C_1$-$C_3$alkyl; n is 1, 2, 3, 4 or 5 and m provides a number average molecular weight of the polymer of from 2000 to 80,000, and the polymer of general formula I or general formula II is provided at a concentration of 0.5 ppm to 30 ppm.

The cosmetic or pharmaceutical compositions can be in any particular form of a composition intended to care for and/or treat ulcerated areas or areas which have suffered cutaneous stress or microstress, brought about in particular by exposure to UV and/or by coming into contact with an irritanant. For example, the composition can be in the form of an aqueous or oily solution, a dispersion lotion, an emulsion (O/W emulsion) or (W/O emulsion), an aqueous or anhydrous gel or cream, and microcapsules or microparticles.

Accordingly, the compositions can be used as a skin care product. For example, a product formulated for a cosmetic, cleansing or protective product for facial or body skin such as an anti-wrinkle or anti-ageing composition for the face; a matt-effect composition for the face; a composition for irritated skin; a make-up-removing composition; a body milk, in particular a moisturizing and optionally after-sun body milk; of an anti-sun composition, or an after-sun care composition, a make-up product for the skin of the face, the body or the lips, such as a foundation, a tinted cream, a blusher, an eye shadow, a free or compact powder, a concealer stick, a cover stick, a lipstick or a lipcare product.

Examples 1 to 5

The following borate buffered formulations were prepared and are reported in Tables 7 and 8. Each formulation includes 0.6 wt. % boric acid, 0.1 wt. % sodium borate about 0.3 to 0.5 wt. % NaCl along with 5 ppm (Ex. No.A) and 10 ppm (Ex. No.B) of each of the exemplary polymeric quaternium compounds. See, Table 7 for the appropriate n value for each of Example Nos. 1 to 4, which correspond to formula I. Example No. 5 is of formula II. Table 8 lists the 4-hour antimicrobial data for each of the solutions.

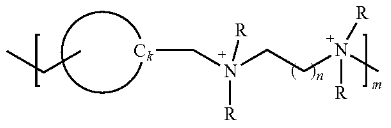
I

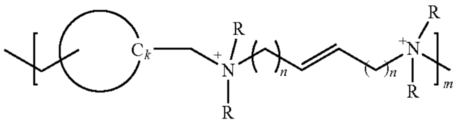
II

TABLE 7

| Example Nos. 1 to 4 | | | | |
|---|---|---|---|---|
| Example | 1 | 2 | 3 | 4 |
| n value | 1 | 2 | 3 | 5 |

Biocidal Stand-Alone Stability

In order to assess the antimicrobial activity of the Example formulations, a "Stand-Alone Procedure for Disinfecting Products" based on the Disinfection Efficacy Testing for Products dated May 1, 1997, prepared by the U.S. Food and Drug Administration, Division of Ophthalmic Devices is used. The stand-alone test challenges the Example formulation with a standard inoculum of a representative range of microorganisms and establishes the extent of viability loss at four hours. The primary criteria for a given disinfection period is that the number of bacteria recovered per mL must be reduced by a mean value of not less than 3.0 logs. The number of mold and yeast recovered per ml must be reduced by a mean value of not less than 1.0 log within the minimum recommended disinfection time with no increase at four times the minimum recommended disinfection time.

The antimicrobial efficacy of each of the various compositions for the chemical disinfection and cleaning of contact lenses are evaluated in the presence of 10% organic soil using the stand-alone procedure. Microbial challenge inoculums are prepared using *Staphylococcus aureus* (ATCC 6538), *Pseudomonas aeruginosa* (ATCC 9027), *Serratia marcescens* (ATCC 13880), *Candida albicans* (ATCC 10231) and *Fusarium solani* (ATCC 36031). The test organisms are cultured on appropriate agar and the cultures are harvested using sterile Dulbecco's Phosphate Buffered Saline plus 0.05 percent weight/volume polysorbate 80 (DPBST) or a suitable diluent and transferred to a suitable vessel. Spore suspensions are filtered through sterile glass wool to remove hyphal fragments. *Serratia marcescens*, as appropriate, is filtered through a 1.2 μm filter to clarify the suspension.

After harvesting, the suspension is centrifuged at no more than 5000×g for a maximum of 30 minutes at a temperature of 20° C. to 25° C. The supernatant is decanted and resuspended in DPBST or other suitable diluent. The suspension is centrifuged a second time, and resuspended in DPBST or other suitable diluent. All challenge bacterial and fungal cell suspensions are adjusted with DPBST or other suitable diluent to $1\times10^7$ to $1\times10^8$ cfu/mL. The appropriate cell concentration may be estimated by measuring the turbidity of the suspension, for example, using a spectrophotometer at a preselected wavelength, for example, 490 nm. One tube is prepared containing a minimum of 10 mL of test solution per challenge organism. Each tube of the solution to be tested is inoculated with a suspension of the test organism sufficient to provide a final count of $1\times10^5$ to $1\times10^6$ cfu/mL, the volume of the inoculum not exceeding 1 percent of the sample volume. Dispersion of the inoculum is ensured by vortexing the sample for at least 15 seconds. The inoculated product is stored at 10° C. to 25° C. Aliquots in the amount of 1.0 mL are taken of the inoculated product for determination of viable counts after certain time periods of disinfection.

The suspension is mixed well by vortexing vigorously for at least 5 sec. The 1.0 mL aliquots removed at the specified time intervals are subjected to a suitable series of decimal dilutions in validated neutralizing media. The suspensions are mixed vigorously and incubated for a suitable period of time to allow for neutralization of the microbial agent. The viable count of organisms is determined in appropriate dilutions by preparation of triplicate plates of trypticase soy agar (TSA) for bacteria and Sabouraud dextrose agar (SDA) for mold and yeast. The bacterial recovery plates are incubated at 30° C. to 35° C. for two to four days. The yeast recovery plates are incubated at 20° C. to 30° C. for two to four days. The mold recovery plates are incubated at 20° C. to 25° C. for three to seven days. The average number of colony forming units is determined on countable plates. Countable plates refer to 30 to 300 cfu/plates for bacteria and yeast, and 8 to 80 cfu/plate for mold except when colonies are observed only for the $10^0$ or $10^{-1}$ dilution plates. The microbial reduction is then calculated at the four hour time point.

TABLE 8

| Example | *S. aureus* | *P. aeruginosa* | *S. marcescens* | *C. albicans* | *F. solani* |
|---|---|---|---|---|---|
| 1A | >5.0 | 4.4 | 4.6 | 2.5 | 2.2 |
| 1B | >5.0 | 4.8 | 4.9 | 3.3 | 3.3 |
| 2A | >5.0 | 4.8 | 4.6 | 2.3 | 0.9 |
| 2B | 5.0 | >4.8 | >4.9 | 2.8 | 1.2 |
| 3A | 3.6 | 4.4 | 3.3 | 1.4 | 1.2 |
| 3B | 3.8 | >4.8 | 3.5 | 1.8 | 1.0 |
| 4A | 4.0 | 3.9 | 3.3 | 1.7 | 0.9 |
| 4B | 4.4 | 4.7 | 3.9 | 2.7 | 0.8 |
| 5B | 4.3 | >4.7 | 4.5 | 3.1 | 0.9 |
| 5C | 4.7 | 4.5 | >4.7 | 3.5 | 1.4 |

Ex. No. 5C contained 20 ppm of the polymeric quaternium compound.

Example 6

A contact lens care solution was prepared according to the formulation represented in Table 9.

TABLE 9

| Component | amount (wt. %) |
|---|---|
| NaCl | 0.36 |
| propylene glycol | 0.20 |
| Tetronic ® 1304 | 0.50 |
| boric acid | 0.64 |
| sodium borate | 0.18 |
| Dequest ® 2016 | 0.10 |
| Example 1 (ppm) | 3 |
| $Na_2EDTA$ | 0.05 |

| BLD 5 ppm RD-2010 | Rabbit Ocular Irritation Screen (4 Hour Test) | |
|---|---|---|
| at pH 7.5 | Weighted Draize Score | Status |
| PV Lens | 0 | Pass |
| Direct Installation | 0 | Pass |

| BLD | | Biocidal Efficacy Screen | | | | |
|---|---|---|---|---|---|---|
| | RD-2010 | 4 Hour Log Reductions with Organic Soil | | | | |
| pH | ppm | *S. aureus* | *P. aeruginosa* | *S. marcescens* | *C. albicans* | *F. solani* |
| 7.5 | 5.0 | >4.8 | >4.7 | 4.5 | 1.3 | 1.9 |
| 7.5 | 2.5 | >4.8 | 4.7 | >4.8 | 1.3 | 1.7 |
| 7.8 | 5.0 | >4.8 | >4.7 | 4.8 | 4.3 | 2.7 |
| 7.8 | 2.5 | 4.8 | >4.7 | 4.8 | 1.9 | 1.6 |

-continued

| | | | | | | |
|---|---|---|---|---|---|---|
| 7.5 | 3.0 | >4.7 | >4.7 | 4.0 | 1.4 | 1.4 |
| 7.8 | 3.0 | >4.7 | 4.7 | 4.6 | 3.8 | 1.5 |

| | Lens Compatibility (mm Average Change) | | | | | | |
|---|---|---|---|---|---|---|---|
| | 1 Cycle | | 7 Cycles | | 30 Cycles | | |
| BLD01 | Change | Reverse | Change | Reverse | Change | Reverse | |
| PureVision | 0.053 | 0.002 | 0.039 | −0.015 | 0.017 | 0.003 | Diam |
| | 0.016 | −0.009 | 0.017 | −0.005 | 0.010 | 0.003 | Sag |
| | 0.030 | 0.012 | 0.015 | −0.008 | 0.004 | −0.001 | BC |
| Oasys | −0.041 | −0.002 | 0.004 | 0.001 | −0.021 | 0.003 | Diam |
| | 0.003 | −0.008 | −0.003 | −0.001 | −0.003 | 0.007 | Sag |
| | −0.040 | 0.008 | 0.008 | 0.002 | −0.016 | −0.005 | BC |
| Acuvue2 | 0.608 | 0.016 | 0.407 | −0.093 | −0.167 | −0.394 | Diam |
| | 0.197 | 0.001 | 0.181 | −0.001 | 0.174 | 0.007 | Sag |
| | 0.329 | 0.013 | 0.170 | −0.080 | −0.307 | −0.347 | BC |

Preparation of Poly[(dimethyliminio)-1,2-ethanediyl (dimethyliminio) methylene-1,4-phenylenemethylene chloride (1:2)]

1,4-Bis(chloromethyl)benzene (17.5 g, 0.1 mol) was added to dry toluene (120 mL) and warmed to 71° C.-72° C. for 5 minutes. $N^1,N^1,N^2,N^2$-tetramethylethane-1,2-diamine (15 mL) was added to this solution and the reaction mixture was stirred at 100° C. under argon atmosphere for 30 minutes. A white precipitate was observed. The heat was turned off and the reaction mixture was allowed to cool over 3 hours with continued stirring to 25° C. The solution was filtered and the recovered solid dried under vacuum at 50° C. for 60 hours to give ~18 g of the crude product with area % HPLC purity >95%.

NMR in $D_2O$ showed the desired product. Using triple detection, it was determined to have Mn of 16,615 and a PD of 1.4

Preparation of polymeric (E)-$N^1$-(4-(chloromethyl) benzyl)-$N^4$-(4-(E)-4-(dimethylamino)but-2-enyl) dimethylammonio) methyl)benzyl)-$N^1,N^1,N^4,N^4$-tetramethylbut-2-ene-1,4-diaminium 1,4-Bis(chloromethyl)benzene (8.75, 0.05 mol) was added to dry toluene (120 mL) and warmed to 60° C.-65° C. for 5 minutes. (E)-$N^1,N^1,N^4,N^4$-tetramethylbut-2-ene-1,4-diamine (15 mL) was added to this solution and the reaction mixture was stirred at 65° C. under argon atmosphere for 10 hours. A white precipitate was observed. The heat was turned off and the reaction mixture was allowed to cool over 3 hours with continued stirring to 25° C. The solution was filtered and the solid was washed with 2×10 mL toluene, dried under vacuum at 50° C. for 60 h to give ~9 g of the crude product with area % HPLC purity >95%. NMR showed the desired product. GPC showed Mn of 2327 and a PD of 1.58

We claim:

1. A contact lens care solution comprising 0.5 ppm to 30 ppm of a polymer of general formula I

I

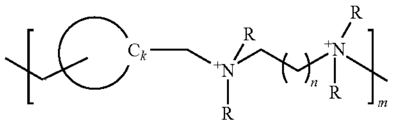

wherein $C_k$ is selected from the group consisting of phenyl, cyclohexyl, cyclohexene, and cyclopentyl;

R is a $C_1$-$C_3$alkyl; n is 1, 2, 3, 4 or 5 and m provides a number average molecular weight of the polymer of from 2000 to 80,000, and a buffer system selected from a borate buffer system, a phosphate buffer system or TRIS, wherein the polymer of formula I is present as the sole antimicrobial component in the solution.

2. The ophthalmic composition of claim 1 wherein R is methyl.

3. The ophthalmic composition of claim 1 wherein $C_k$ is phenyl, R is methyl, and n is 1 or 2.

4. The ophthalmic composition of claim 1 wherein $C_k$ is phenyl, n is 1 and m provides a number average molecular weight of from 4000 to 40,000.

5. The lens care solution of claim 1 further comprising a biopolymer selected from the group consisting of hyaluronic acid, alginic acid, hydroxypropyl guar and hydroxypropylmethyl cellulose; and a nonionic surfactant selected from a poloxamer, poloxamine or a mixture of the two.

6. The lens care solution of claim 5 wherein the biopolymer is hyaluronic acid, the hyaluronic acid provided at a concentration of 0.005 wt. % to 0.05 wt. %.

7. The lens care solution of 5 wherein the number average molecular weight of the polymer of formula I is from 4000 to 24,000.

8. The lens care solution of 5 wherein the polymer of formula I is present in the composition at a concentration of 0.5 ppm to 10 ppm.

9. The lens care solution of 5 wherein the solution satisfies primary biocidal kill in that for a recommended disinfection period the number of bacteria recovered per mL is reduced by a mean value of not less than 3.0 logs, and the number of mold and yeast recovered per mL is reduced by a mean value of not less than 1.0 log within the recommended disinfection period.

10. The ophthalmic composition of claim 1 wherein the polymer of formula I is present in the composition at a concentration of 0.5 ppm to 10 ppm.

* * * * *